(12) United States Patent
Bauman

(10) Patent No.: US 8,397,911 B1
(45) Date of Patent: Mar. 19, 2013

(54) ASYMMETRICAL LOCKING TUBE

(76) Inventor: Todd J. Bauman, Plymouth, MN (US)

( * ) Notice: Subject to any disclaimer, the term of this patent is extended or adjusted under 35 U.S.C. 154(b) by 0 days.

(21) Appl. No.: 13/563,304

(22) Filed: Jul. 31, 2012

(51) Int. Cl.
*B65D 85/20* (2006.01)
(52) U.S. Cl. .................. 206/364; 242/172; 24/16 R
(58) Field of Classification Search .............. 206/363, 206/364, 438, 53; 242/159, 172; 24/16 R; 604/159, 264; 600/585
See application file for complete search history.

(56) References Cited

U.S. PATENT DOCUMENTS

| | | | | |
|---|---|---|---|---|
| 4,607,746 A * | 8/1986 | Stinnette | ......................... | 206/53 |
| 5,217,114 A * | 6/1993 | Gadberry et al. | ............. | 206/364 |
| 5,344,011 A * | 9/1994 | DiBernardo et al. | ......... | 206/364 |
| 6,375,006 B1 * | 4/2002 | Samuels | ....................... | 206/364 |
| 7,461,741 B2 * | 12/2008 | State et al. | ..................... | 206/364 |
| 2005/0205446 A1 * | 9/2005 | Duffy et al. | .................... | 206/364 |
| 2005/0256501 A1 * | 11/2005 | Rispens | ........................ | 604/523 |
| 2009/0018633 A1 * | 1/2009 | Lindquist et al. | ............ | 623/1.11 |
| 2012/0031792 A1 * | 2/2012 | Petit | .............................. | 206/438 |

* cited by examiner

*Primary Examiner* — Jacob K Ackun
(74) *Attorney, Agent, or Firm* — Moss & Barnett

(57) ABSTRACT

A protective tubing assembly having male and female connectors integrally formed along its exterior surface and an asymmetrical cross-section with additional wall thickness in the non-connector cross section regions is provided by the present invention. Cooperating, substantially flat exterior bearing surfaces may also be formed along the exterior surface of the tubing. The tubing can be wound into coiled alignment with the male and female connectors securing adjacent coils together, and the additional wall thickness regions in the asymmetrical cross-sectional reducing unwanted twisting of the tubing that would otherwise lead to individual coils rising from their original, substantially planar coiled alignment. An extrusion manufacturing process with special inner and outer dies is also provided.

19 Claims, 8 Drawing Sheets

ASYMMETRICAL LOCKING TUBE

FIELD OF THE INVENTION

This invention relates generally to hollow protective tubing for the storage, transportation, and handling of medical catheters and guidewires, and more specifically to tubing with integral connectors that can be coiled upon itself without twisting and lifting while preventing damage to the medical device contained therein.

BACKGROUND OF THE INVENTION

The heart represents a critical organ for pumping blood through the human or animal body. This blood delivers food and oxygen through the arteries to all of the body's cells, while carrying away waste. The heart also needs a constant oxygen supply for proper functioning.

Coronary artery disease is caused by atherosclerosis when deposits of fat, calcium, and dead cells collect along the inner layers of the artery walls. The resulting plaques narrow the arteries to interfere with the smooth flow of blood. A blood clot (thrombus) can block the artery to stop the passage of blood entirely. If this occurs within a coronary artery, a heart attack may result. A blood clot formed in an artery in the brain may cause a stroke.

Electrocardiographs can be used by physicians to display the electrical activity of the heart. A poor electrocardiograph suggesting the presence of coronary heart disease may prompt the physician to administer a cardiac catherization in which a long, flexible tube called a "catheter" is inserted through an artery in the patient. An injected dye will clearly show the condition of the arteries as the dye travels in the blood through them, as captured by an angiogram X-ray.

While coronary heart disease patients are typically treated by drugs and dietary and exercise regimens, this may be insufficient for some patients. For such patents, a coronary angioplasty may be administered where a catheter with a small deflated balloon attached to its end is inserted into the narrowed area of the artery. By carefully inflating the balloon to push the plaque against the arterial wall, the artery can be enlarged and opened. Proper blood flow can be restored, in more serious cases, tiny metal tubes called stents may be placed in the damaged area of the artery to prop it open.

Catheters may be used in conjunction with other medical devices besides balloon catheters for angioplasties. For example, catheters may apply suction to the bladder or kidneys to drain urine, or administer intravenous fluids like medicines, epidurals, and nutritional supplements. Catheters may also be used by physicians to guide endoscopes with a camera for examining the interior of organs, or lasers for treating veins and organs.

Because catheters must be extremely small in cross section to pass through blood vessels, they are necessarily fragile. A range of polymers like silicone rubber, latex, and thermoplastic elastomers are commonly used to make catheters because these materials are inert and unreactive to body fluids and medical fluids into which they will come into contact during medical procedures. But, such materials are also weak mechanically, and may fracture during handling, transport, or storage.

Thus, catheters and guidewires typically must be contained in protective tubes during storage, transport, and usage. These tubes represent long, hollow bodies made from polymers like high-density polyethylene ("HDPE") or low-density polyethylene ("LDPE") which provide impact protection along with required flexibility. The interior diameter of these protective tubes typically are very small for accommodating catheters and guidewires while preventing them from moving too much within the tubes. But, because catheters and guidewires may need to be one foot or longer for medical procedures, these protective tubes must be at least that long.

A need exists therefore within the medical industry for these protective tubes containing medical devices to be coiled, so that they can be managed more easily during medical procedures, and stored and transported in confined spaces. Once coiled, the catheter, guidewire, or other medical device can be threaded through the protective tube.

External mechanical clips are commonly used within the industry to secure catheter or guidewire protective tubing in coiled alignment. U.S. Pat. No. 6,375,006 issued to Samuels, for example, discloses a flat clamp piece containing multiple vertically-aligned holes. Flexible tubing for catheter guidewires must be threaded through corresponding holes in the clips to form a stacked coil with several of these clamps positioned along the circumference of the coiled tubing. While this type of clamp fits around the entire tube, it does not allow the tube to be removed from the clamps very easily. Moreover, these clips allow the individual coils of the tube to rotate with respect to each other out of a flat planar coiled alignment.

A different type of clamp is shown in U.S. Pat. No. 7,104,399 issued to Duffy et al. and U.S. Published Application 2008/0006554 filed by Duffy et al., featuring open-faced clamp with multiple side-by-side channels. The tubing can be press fitted into the channels of a clip with a plurality of these clamps positioned along the circumference of the coiled tubing to form a coil in which multiple windings of the tube are positioned side-by-side. While this type of clamp allows coils of different diameter to be formed, and enables a user to release the tubing from the clamps and then reform a coil of different diameter, the clamps can accidentally become disengaged from the tubing during transport, storage, or handling.

U.S. Published Application 2011/027186 filed by Enns et al. discloses another embodiment of packaged elongated medical devices in which catheter tubing is coiled with multiple windings at the factory and secured in place in a mold. Plastic is then injected into the mold to form permanent clips at predetermined points around the coil circumference. While more secure than the open-faced mechanical clamp because such clips bond to the tubing outer wall, the catheter tubing cannot be separated from these integrally molded clips to adjust the tubing in the field.

U.S. Pat. No. 7,461,741 issued to State et al. shows yet another arrangement for tubing for a catheter or guide wire featuring a closed channel with a "C-shaped" open channel extending from its outer surface. While the catheter or guidewire can be passed through the closed channel, the tube may be snap-fitted into the C-shaped open-channel to form a side-by-side aligned coil.

U.S. Pat. No. 5,344,011 issued to DiBernardo et al. illustrates a package assembly comprising multiple housing units. Each housing contains several channels for receiving a coiled catheter tube winding to align the tube in a secured coil. A T-shaped channel at the bottom of the housing accommodates the T-shaped prong of a separate movable housing unit with an interior channel for accommodating the end of the tube. In this manner, the physicians can slide the tube end along the exterior of the wound coil during a surgical procedure to advance the catheter.

While all of these types of mechanical clamps will secure a catheter tube into a wound coil, they are cumbersome to install around the tubing, and in some cases become easily dislodged in the field. This may result in unwinding of the tube and possible damage to the catheter inside it in the operating room or field. Moreover, the mechanical clips allow the tubing often to twist with respect to the fixed mechanical clamps to allow the windings to rise up with respect to each other from the original planar coiled alignment. This may compound the damage to the medical devices contained inside the tubing, and interfere with the sterile packaging containing the coiled tubing.

It is known within the electrical cord or electrical wire industry to include beads and grooves along the exterior of the insulative casing. The casing with the electrical conductors contained inside can be wound into a coil or stack-looped arraignment with the beads snapped into the cooperating grooves to secure the cord or wire in alignment. Separate mechanical clamps are unnecessary. See, e.g., U.S. Pat. Nos. 2,888,511 issued to Guritz; 6,751,382 issued to McGarvey, and 7,574,778 issued to Marathe. However, solid wire conductors with an equally solid insulative coating around its exterior surface can be more readily coiled and snapped into alignment without worrying about possible damage to the conductor. A hollow catheter tube, on the other hand, can easily be kinked during the coiling process with resulting damage to the catheter contained inside the tube.

U.S. Pat. No. 4,607,746 issued to Stinnette discloses a flexible elongated tube for holding a medical guidewire. The tubing features cooperating projections and C-shaped channels extending from opposite points on the exterior of the tube. The tubing may be wound into a coil with the projections pressed into the mating channels. But, because the tubing of Stinnette is perfectly circular in cross section, the resulting tube coils may twist and easily rotate with respect to the fixed connection points. This allows the windings in the tubing to rise up from their original planar coiled alignment during transport, storage, or handling, and result in the coil becoming unsecured. This is a particular problem for medical devices like catheters or guidewires where they have been sterilized, coiled, and placed in sanitary packaging at the factory. If the coil becomes unsecured inside the package, it cannot be resecured in coiled alignment without opening the sanitary package. The catheter or guidewire can also become damaged inside the unraveling coils. This is why, in part, the medical device industry relies upon separate external clamps for securing protective tubing into coiled alignment in spite of the cumbersome assembly and expense of the clamps.

Therefore, providing a protective tubing assembly for containing medical devices or other long, thin fragile products that can be wound into a coil, and retained via cooperating male and female connectors integrally formed along the exterior of the tubing in a substantially flat planar alignment would be advantageous. Such a coiled tubing should inhibit individual coils from rotating with respect to each other, or rising from the substantially flat planar alignment that can cause the tubing to become unwound inside its packaging or during handling, and damage the medical device or long, thin fragile product contained therein.

SUMMARY OF THE INVENTION

A protective tubing assembly for containing a medical device or other long, thin, fragile object with the tubing featuring cooperating male and female connectors, and an asymmetrical cross-section with additional wall thickness in the non-connector cross section regions is provided by the present invention. Cooperating, substantially flat bearing surfaces may also be formed along the exterior surface of the tubing. The tubing can be wound into coiled alignment with the male and female connectors securing adjacent coils together, and the additional wall thickness regions in the asymmetrical cross-sectional reducing unwanted twisting of the tubing that would otherwise lead to individual coils rising from their original, substantially planar coiled alignment. Substantially flat bearing surfaces formed along respective abutted portions of the tubing coils also provide stable, non-rotational alignment of the wound tubing. Alternatively, the cooperating substantially flat bearing surfaces may be formed along the exterior surface of the tubing where the male projecting connector joins the tubing, and the outside of the female receiving connector. Such a protective tubing assembly can be used to house a catheter, guidewire, or other long, thin fragile object in a stable, sanitary environment, and prevent the coil from becoming unwound inside its packaging or during handling to avoid damage to the medical device or other object contained inside the tubing.

The protective tubing assembly is produced by means of an extrusion process from high-density polyethylene, low-density polyethylene, or a blend thereof. It has been surprisingly discovered that an oblong-shaped outer extrusion die in combination with an oblong-shaped inner die rotated 90 degrees to the longitudinal axis of the outer die will produce the asymmetrical cross section of the tubing body having an oblong outer diameter and a round, inside diameter. The cylindrical inner bore is ideal for containing the catheter, guidewire, or other long, thin fragile object without binding or damage.

BRIEF DESCRIPTION DRAWING

DETAILED DESCRIPTION OF THE PREFERRED EMBODIMENT

A protective tubing assembly for containing a medical device or other long, thin, fragile object with the tubing featuring cooperating male and female connectors, and an asymmetrical cross-section with additional wall thickness in the non-connector cross section regions is provided by the present invention. Cooperating, substantially flat bearing surfaces may also be formed along the exterior surface of the tubing. The tubing can be wound into coiled alignment with the male and female connectors-securing adjacent coils together, and the additional wall thickness regions in the asymmetrical cross-sectional reducing unwanted twisting of the tubing that would otherwise lead to individual coils rising from the original planar coiled alignment. The bearing surfaces along respective abutted portions of the tubing coils also provide stable, non-rotational alignment of the wound tubing. Such a protective tubing assembly can be used to house a catheter, guidewire, or other medical device in a stable, sanitary environment, and prevent the coil from becoming unwound inside its packaging or during handling to avoid damage to the medical device or other object contained inside the tubing.

In the context of the present application, "medical device" means any hollow catheter tube to be inserted into a blood vessel of a human or animal to remove fluids or administer fluids or medicines during a medical treatment or medical procedure, or any other surgical device passed through the catheter for purposes of a medical procedure, including but limited to a catheter, guidewire, endoscope or laser, camera, or other surgical tool.

For purposes of the present invention, "medical procedure" means any minimally invasive surgical procedure performed on an organ of the human or animal body, including but not limited to a cardiac catheterization, coronary angioplasty, internal examination of a heart, bladder, vein, artery, brain, or other organ via an endoscope, vascular ablation performed by a laser or surgical procedure performed by a surgical tool.

As used in this Application, "protected object" means any medical device or other long, thin, fragile object stored, transported, or used with the protective tubing assembly of this invention.

Although the protective tubing assembly has applications to many varied medical devices and protected objects, for illustrative purposes only, the invention is described herein with respect to a medical catheter. The protective tubing assembly, however, may be utilized to contain any elongated flexible object capable of being coiled upon itself that is used inside or outside the medical industry. The protective tubing assembly therefore should not be interpreted to be limited to a protection of medical catheters.

Figure 1:
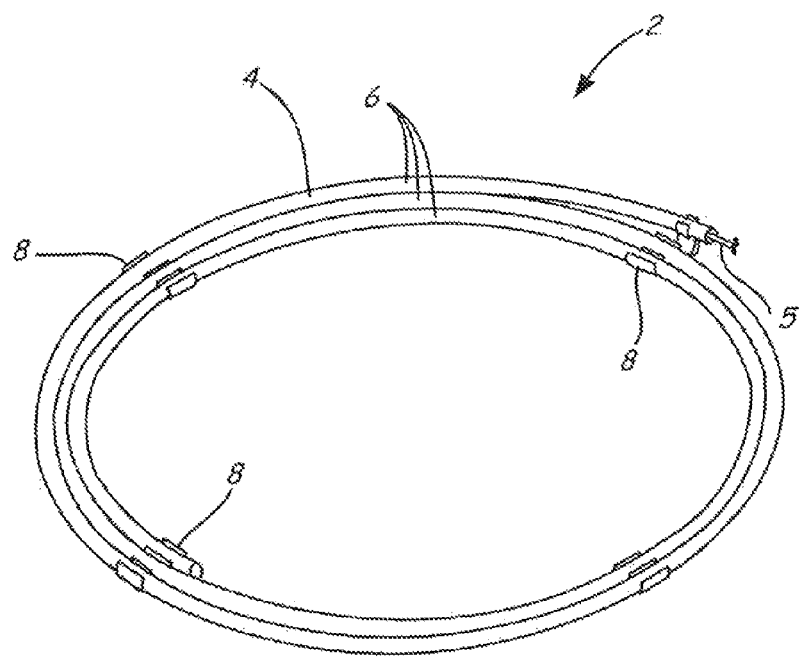
FIG. 1 is a perspective view of a coiled tubing secured by external mechanical clips practiced in the prior art.

The prior art embodiment 2 discussed above for the coiled alignment of a tubing 4 for a catheter 5 with its windings 6 secured by a plurality of external clips 8 is shown in FIG. 1.

Figure 2:
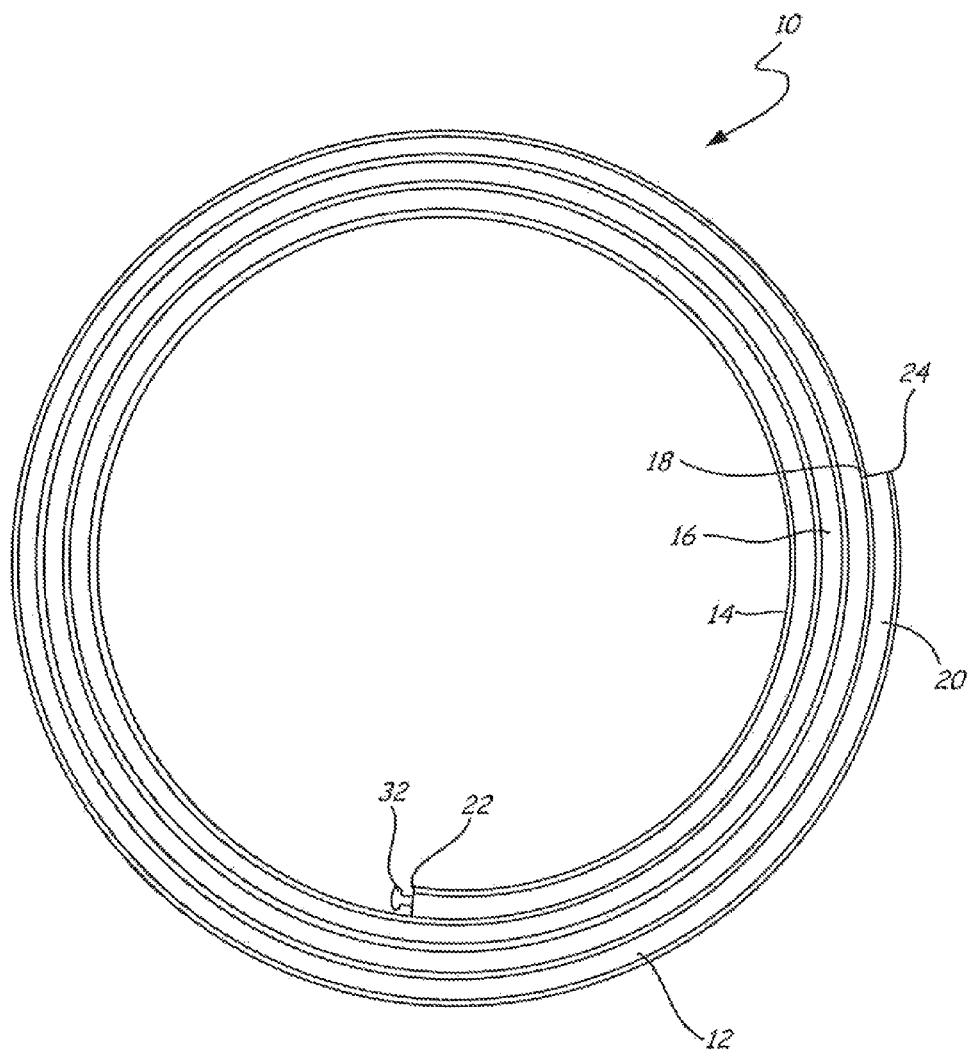
FIG. 2 is a plan view of the locking tube 10 of the present invention in coiled alignment.
Figure 3:
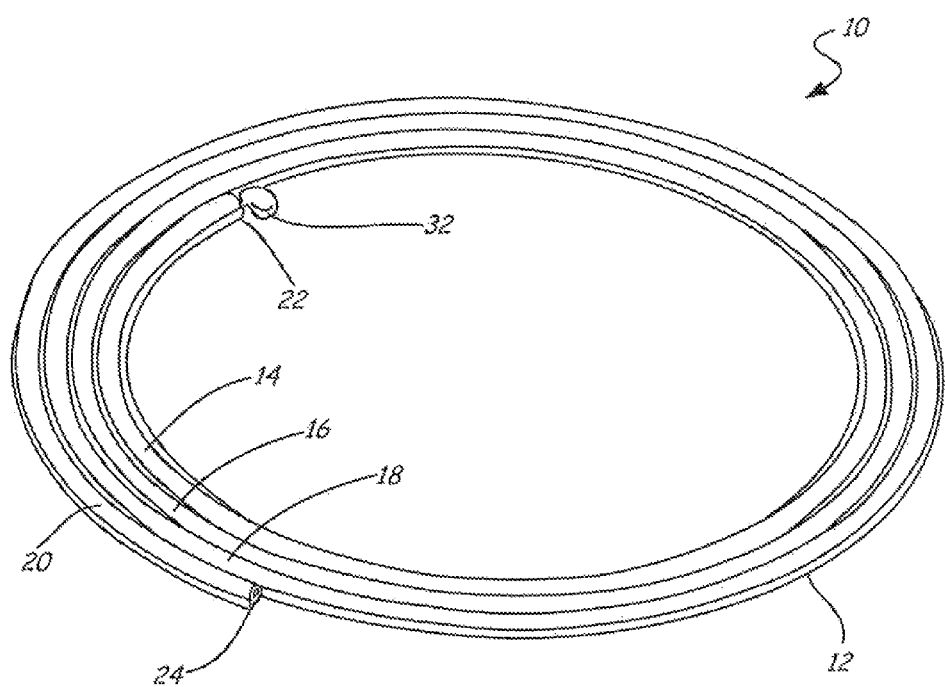
FIG. 3 is a perspective view of the locking tube 10 of the present invention in coiled alignment.

The protective tubing assembly 10 of the present invention that can be locked upon itself to provide a secure, planar, and stable coiled alignment is shown in FIGS. 2 and 3. It comprises a flexible hollow tube body 12 that is capable of being coiled into multiple concentric coils 14, 16, 18, and 20. While tubular body 12 is shown in FIGS. 1 and 2 with four coils, any larger or smaller number of coils is possible. Tubular body 12 has a first end 22 and a second end 24. It also contains an outer wall 26 and an inner wall 28 defining a hollow bore 30 running the entire length of tube 12. First end 22 may be heat sealed shut to prevent passage of dirt or other contaminants inside bore 30. Alternatively, first end 22 may be closed by means of removable plug 32. Second end 24 of tube 12 will be open to accept insertion of the catheter or other medical device 34 into bore 30 for protection from kinking, breakage, or other damage. This second end 24 may then be closed of by means of a removable plug 36. Alternatively, it may have secured thereto a nipple or other fitting appropriate for the medical device to which the catheter 34 is to be operatively secured.

Figure 4:
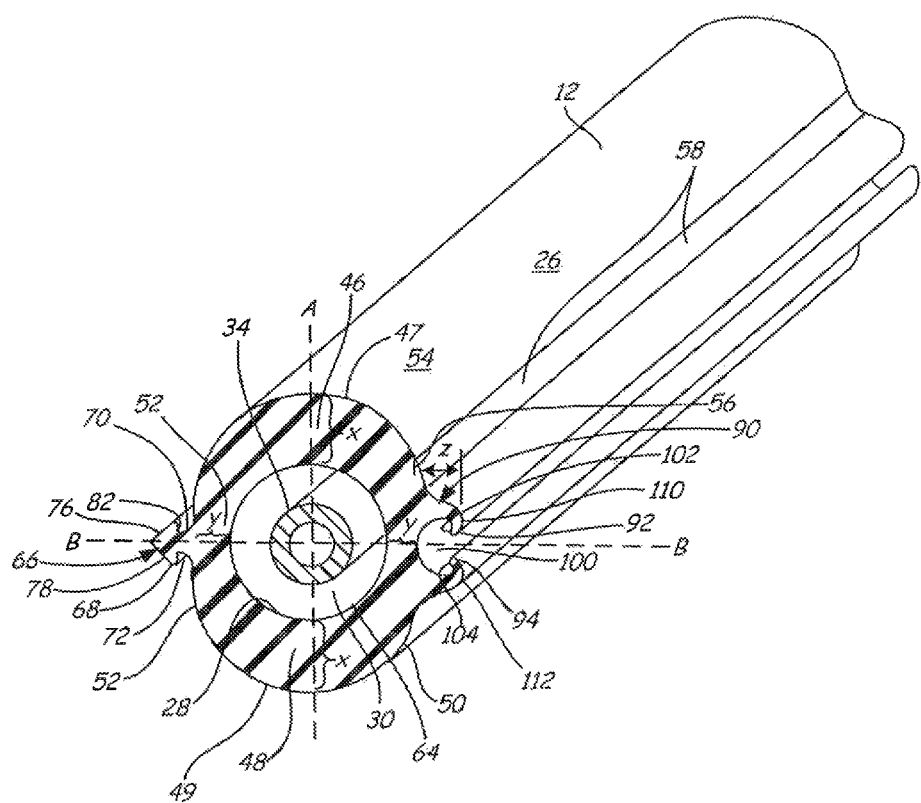
FIG. 4 is a perspective, cut-away view of the locking tube 10 showing its cross-sectional shape and features.

A length of tubing body 12 is depicted in FIG. 4 in a straight, unwound configuration. Outer wall 26 provides exterior protection against exterior forces, chemical penetration, or other contamination. Inner wall 28 defines a cylindrical inside bore 30 having a circular cross section. Catheter 34 passes inside bore 30 in a protected state.

In an important feature of the present invention, tubular body 12 of protective tubing assembly 10 bears an asymmetrical circular cross section. Instead, as shown more clearly in FIG. 4, the cross section of tubular body 12 is oblong in shape positioned along a longitudinal axis A-A and a transverse axis B-B.

The outside diameter of the tubing along the longitudinal axis A-A is larger than the outside diameter along the transverse axis B-B. Because this inside bore 30 of the tubing is substantially circular in cross-section, the resulting annulus of the tubing exhibits a larger wall thickness X in the arcuate, non-connecting cross-sectional regions 46 and 48 along the longitudinal axis A-A, compared with the wall thickness Y in the connecting cross-sectional regions 50 and 52 along the transverse axis B-B.

Arcuate exterior body surface 54 of the tubing body outer wall 26 is defined by the top arcuate portion 47 of the cross-sectional circumference along longitudinal axes A-A (as shown in FIG. 3). A similar arcuate exterior body surface 56 of the tubing body outer wall 26 is defined by the bottom arcuate portion 49 of the cross-sectional circumference, along longitudinal axis A-A (see FIG. 5). Similarly, exterior body surface 58 of the tubing body outer wall is defined by the right-hand portion 50 of the cross-sectional circumference along transverse axis B-B. Exterior body surface 60 is defined by the left-hand portion 52 of the cross-sectional circumference along transverse axis B-B.

The interior wall 62 forms substantially cylindrical-shaped bore 30 defined by substantially circular, cross-sectional circumference 64. Bore 34 is preferable substantially cylindrical in shape, although it will be appreciated that shapes other than a cylinder are possible for bore 30, especially if the protected object to be stored in the protective tubing assembly 10 does not bear a cylindrical shape. Nevertheless, because catheters, guidewires, and other medical devices do commonly bear a cylindrical shape, an internal bore 30 that is substantially cylindrical in shape is preferred for purposes of the protective tubing assembly 10 of the present invention.

Extending from at least a portion of exterior body surface 60 of tubular body 12 along transverse axis B-B is male projection connector 66. This male projection connector 66 may adopt any of a number of possible three-dimensional shapes. In the preferred embodiment of the present invention, it exhibits an "arrow" profile bearing throat portion 68 defining lateral surfaces 70 and 72, "head" portion 74 defined by leading surfaces 76 and 78 forming an obtuse angle meeting at leading edge 80, and bearing surfaces 82 and 84 disposed respectively between leading surfaces 76 and 78 and lateral surfaces 70 and 72. The lateral surfaces and bearing surfaces of male projection connector 66 and flat body portions 58 and 60 cooperate to form recess channels 86 and 88.

Extending from at least a portion of exterior body surface 58 of tubular body 12 along transverse axis B-B, and opposite to male projection connector 66, is female receiving connector 90. This female receiving connector 90 may adopt any of a number of possible three-dimensional shapes. In the preferred embodiment of the present invention, it exhibits a "C-shaped" profile bearing curved finger extensions 92 and 94 terminating in lips 96 and 98, respectively. The interior surfaces of finger extensions 92 and 94, lips 96 and 98, and a portion of exterior body surface 58 of tubular body 12 cooperate to define arcuate surface 100, bearing surfaces 102 and 104 and reception channel 106.

Figure 5:
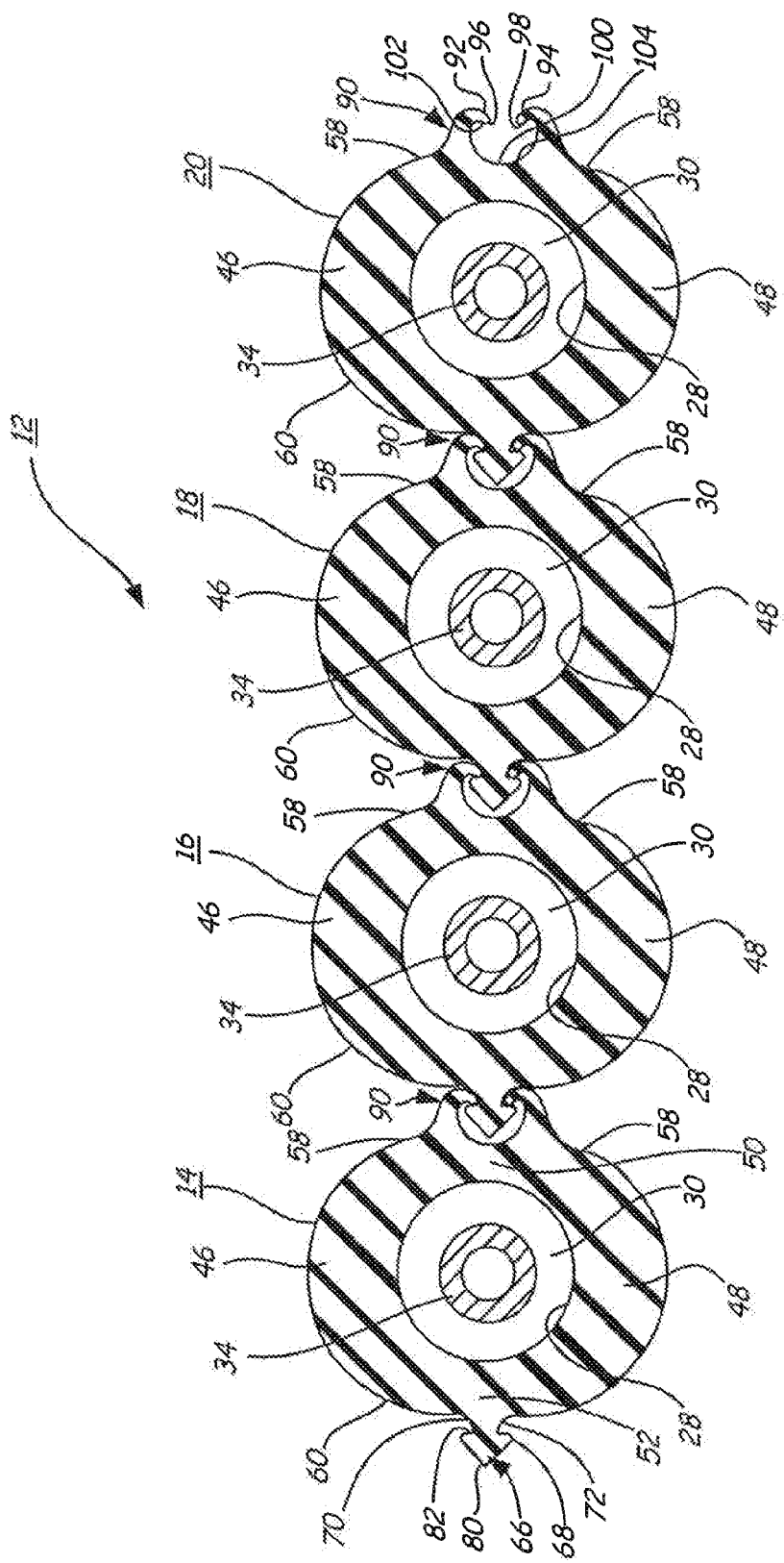
FIG. 5 is an end view of four portions of the locking tube connected to each other via their respective male and female connectors to form a wound coil.

The adjacent side-by-side aligned coil windings 14, 16, 18, and 20 of protective tubing assembly 10 are shown more clearly in FIG. 5. Male projection connector 66 on tubular winding coil 16 snap fits into female receiving connector 90 on tubular winding coil 14. Likewise, male projection connector 66 on tubular winding coil 18 snap fits into female receiving connector 90 on tubular winding coil 16, and male projection connector 66 on tubular winding coil 20 snap fits into female receiving connector 90 on tubular winding coil 18.

Figure 6:
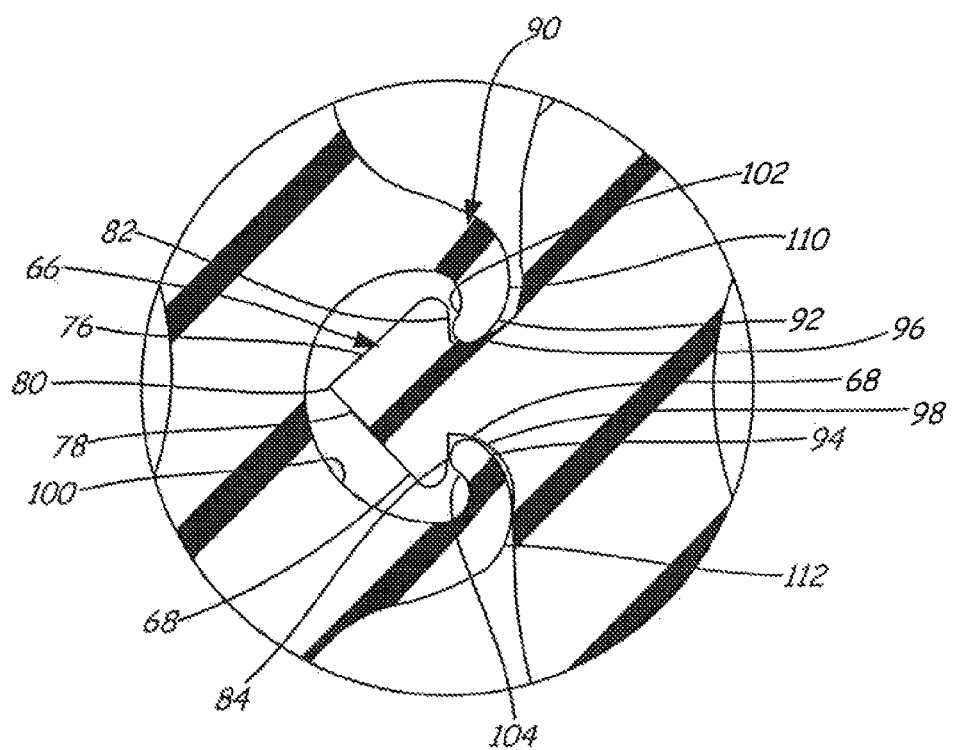
FIG. 6 is an expanded view of a connected male connector and female connector shown in FIG. 5.

As shown more clearly in FIG. 6, upon insertion of male projection connector 66 into reception channel 106 of female receiving connector 90, leading edge 80 of male projection connector 66 passes between lips 96 and 98 of female receiving connector 90. Because leading surfaces 76 and 78 are slanted back from leading edge 80, they bias lips 96 and 98 in an outwardly direction as the lips 96 and 98 slide along the leading surfaces 76 and 78 to open female receiving connector 90.

Once the lips 96 and 98 travel beyond the leading surfaces 76 and 78 to allow the entire male projection connector 66 to pass inside the reception channel 106 of female receiving connector 90, lips 96 and 98 will return to their original configuration due to the "memory" of the plastic material used to form the female receiving connector 90. Lips 96 and 98 fit inside recess channels 86 and 88 in male projection connector 66, so that hearing surfaces 82 and 84 of male projection connector 66 interact with the lips of 96 and 98 of female receiving connector 90 to prevent the male projection connector 66 from being pulled out of reception channel 106 of female receiving connector 90. In this manner, adjacent coil windings 14 and 16, 16 and 18, and 18 and 20 will remain securely connected to each other without unwanted separation during the storage, transport, or handling of catheter 34 inside protective tubing housing 10. The male projection connector 66 and female receiving connector 90 integrally formed along the exterior surfaces 58 and 60 of the tubular body 12 providing this connective means without the need for the cumbersome and unreliable external clips of the prior art.

The dimensions of female receiving connector 90 and male projection connector 66 are defined with respect to each other so that they provide a close and secure means of connection of the adjacent coil windings of tubular bodies 12 that cannot become easily detached. At the same time, the dimensions should be such that a user can snap fit the male projection connector 66 into engagement with the female receiving connector 90 without an unreasonable amount of force. In a preferred embodiment, the closely-fitted dimensions of the male projection connector 66 and female receiving connector 90 will cause an audible snapping sound as the male projection connector 66 is inserted into the receiving reception channel 106 of female receiving connector 90 to confirm to a user that the adjacent coils have been successfully connected to each other.

While the arrowhead and C-cup shapes are preferred for the male projection connector 66 and female receiving connector 90 of the present invention, other shapes and configurations are possible. For example, the projection head of the male connector 66 can instead bear the shape of a half circle, half moon, half star, or square or rectangle, instead of a triangle, with the leading edge biasing the lips of the female connector 90 in the manner described above. At the same time, the female receiving connector 90 can bear any shape other than a C-cup as long as it provides flexible lips that can be biased outwardly by the male connector had to accept insertion of the male connector, followed by an automatic return of the fingers to substantially their original configuration to engage a surface of the male connector 66 to prevent its accidental separation from the female connector 90.

The inside diameter of the bore 30 of tubular body 12 is 0.07-0.15 inches for catheters, preferably 0.085-0.13 inches, more preferably 0.09-0.12 inches. Where the protective tubing assembly 10 is to contain guidewires, the inside diameter forming the bore 30 should be 0.095-0.103 inches.

The outside diameter of the tubular body along the longitudinal axis A-A should be 0.10-0.175 inches, preferably 0.11-0.16 inches. The outside diameter of the tubular body along the transverse axis B-B (not counting the male projection connector 66 and female receiving connector 90) should be 0.09-0.15 inches, preferably 0.08-0.15 inches.

The wall thickness X along the longitudinal axis A-A should be at least 0.035 inches, preferably 0.035-0.105 inches more preferably 0.05-0.10 inches. The wall thickness Y along the transverse axis B-B should be 0.049-0.053 inches, preferably 0.050-0.052 inches.

The increased wall thickness X with respect to wall thickness Y of tubular body 12 comprises an important feature of this invention. The increased wall thickness X along the longitudinal axis A-A helps to reduce or prevent tubular body 12 from twisting or otherwise deforming with respect to the connection points between adjacent coil windings along transverse axis B-B. This will substantially help to reduce or prevent the coil windings from rising from their original, substantially planar coiled alignment.

The distance between adjacent connected coil windings of tubular body 12 will substantially be defined by the lateral distance Z that female receiving connector 90 extends from exterior tubular surface 58. This distance Z needs to be large enough to enable an adequately-sized reception channel 106 inside the female receiving connector 90 for accommodating male projection connector 66. At the same time, distance Z needs to be small enough to enable adjacent connected tubular body coil windings to be close enough to provide stability. Rotation of one coil winding with respect to an adjacent coil winding is undesirable since it may lead to the windings rising up from the original, substantially planar coiled alignment or the adjacent coils becoming accidentally separated from each other. It is therefore, preferred that adjacent connected tube windings be in "close proximity" with each other. This close proximity is defined by distance Z for the projection of female receiving connector 90 from exterior surface 58 of tubular body 12 being 0.093-0.099 inches, preferably 0.01-0.08 inches, more preferably 0.02-0.07 inches.

In another feature of the invention, exterior body surface portion 60 of tubular body 12 near the male projecting connector 66 should be substantially flat. This substantially flat exterior body surface should be oriented substantially parallel to the longitudinal axis A-A. Exterior body surface 58 may also be substantially flat and substantially parallel to longitudinal axis A-A. In this manner, when adjacent coil windings of tubular body 12 are connected to each other via their respective male projection connector 66 and female receiving connector 90, the substantially flat exterior surface 60 of one tubular body 12 will be closely adjacent to or even abut the substantially flat exterior body surface 58 of the other tubular body to help to reduce rotational movement of the one tubular body with respect to the other tubular body. This will provide greater stability to the coiled tubing.

In an alternative embodiment, the exterior surfaces 110 and 112 of fingers 96 and 98 of female receiving connector 90 may be substantially flat. When adjacent tubular bodies 12 are connected to each other via male projection connector 66 and female receiving connector 90, these substantially flat exterior surfaces 110 and 112 on female connector 90 will be closely adjacent to or even abut the substantially flat exterior surface 60 of the adjacent tubular body 12 to provide this added stability to the coiled tubing.

In another embodiment, the male projecting connector 66 and/or female receiving connector 90 that are integrally formed along the exterior of the tubing body 12 may have cuts added approximately every 1.50-2.50 inches to form a plurality of male projecting connectors and/or female receiving connectors to make it easier to bend the protective tubing assembly 10 into a coiled arrangement.

Figure 7:
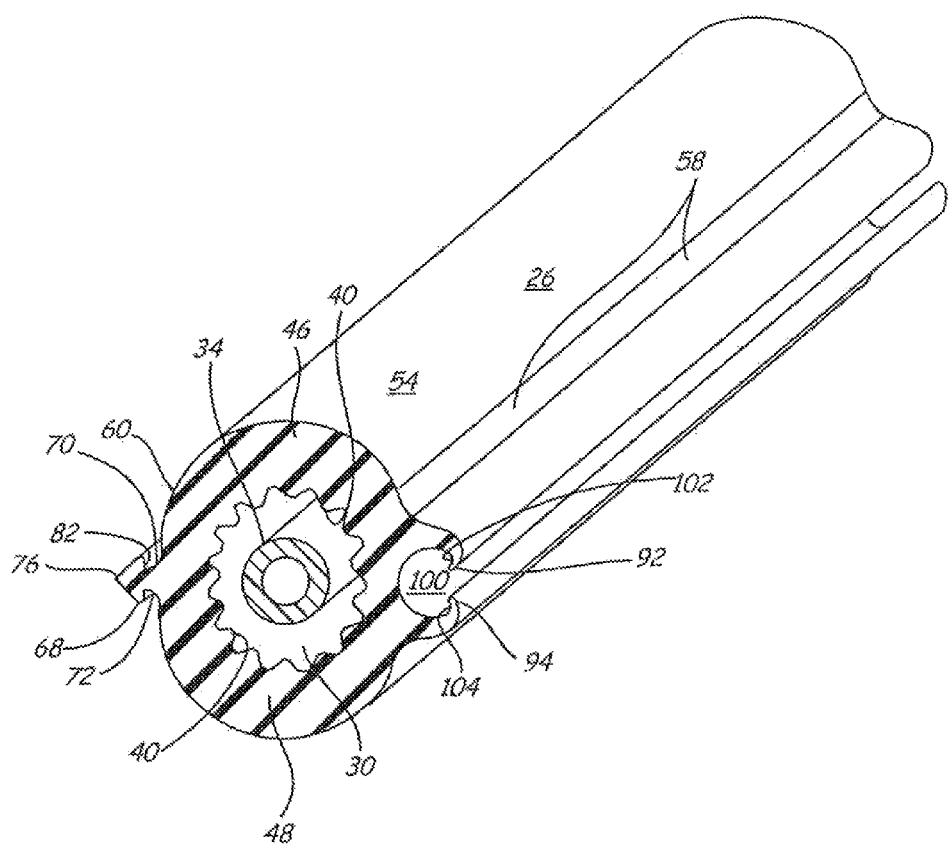
FIG. 7 is a perspective, cut-away view of the locking tube with a plurality of ribs formed along the interior surface of the tube.

As shown in FIG. 7, a plurality of ribs 40 may be formed along inner wall 28 to provide reduced contact points between inner wall 28 of tube 12 and the exterior surface of catheter 34 in order to reduce frictional forces as the catheter is inserted inside tube body 12. If desired, ribs 40 may be coated with a suitable lubricant material 1 to further reduce these frictional forces in cases where the inside diameter of bore 30 provides a close fit with the exterior surface of catheter 34.

A portion of first end 22 or second end 24 of tubular body 12 may be skived to allow for external tools to be easily connected to the tube by the physician or technician. This skiving will reduce the outside diameter of the tubular body. The skived region 110 may extend 0.0-2.0 inches from the end of the tubing. This skived region 110 may also extend into the tubular body from the external surface diameter where necessary to accommodate the dimensions of an adaptor for a medical device or tool.

The tubular bodies 12 and their integral male projection connectors 66 and female receiving connectors 90 may be made from any suitable polymer material that provides a required degree of flexibility to the tubing so that it may be coiled, while protecting the catheter or other protected object contained therein from impact forces that can damage or break it. High density polyethylene ("HDPE") is commonly used within the industry for protective tubes for catheters because of its relatively low cost, and has rigid strength to protect its content. HDPE polymer resins are widely available in the market from a variety of suppliers. Thus, HDPE polymer can be used to produce the protective tubing assembly 10 of the present invention.

Alternatively, the protective tubing assembly 10 may be produced from low-density polyethylene ("LDPE"). LDPE polymer resins are also widely available from a variety of suppliers in the marketplace. LDPE polymers are more flexible than HDPE polymers, although they are also more expensive than HDPE polymer resins. At the same time, LDPE polymers do not exhibit as much slipperiness as HDPE polymers do.

in a preferred embodiment of the present invention, the protective tubing assembly 10 may be produced from a blend of HDPE and LDPE polymer resins, such as a 50% HDPE/50% LDPE blend. Such a blend can yield a polymer material for the protective tubing assembly that is cheaper than pure LDPE polymer, while being more flexible than pure HDPE polymer, but stiffer than pure LDPE polymer.

in yet another preferred embodiment, the protective tubing assembly 10 can be made from a polymer co-extrusion having a HDPE inner core that provides impact resistance to protect the catheter stored inside the tubular body 12, along with a degree of lubrication for assisting in the insertion of the catheter into and removal of it from the bore 30 in the tubular body. Meanwhile, a LDPE outer core of the co-extrusion will provide greater flexibility to the male projection connector 66 and female receiving connector to enable them to mate with each other more easily.

Another possibility is to employ a polymer co-extrusion with HDPE polymer for the inner core, and a blend of HDPE/LDPE polymer for the outer core and connectors. A person of ordinary skill in polymer materials will understand how to choose the correct HDPE and LDPE materials and blends thereof to take advantage of their physical and performance characteristics.

The protective tubing assembly 10 of the present invention is produced by means of an extrusion process. Extrusion is a continuous process where the solid polymeric resin material in the form of pellets or powders is sheared and heated as they are conveyed through either a single or twin-screw extruder to become a pressurized melt of polymeric material. The rotating screws are used inside the heated barrel of the extruder to force the plastic through the barrel to an extrusion die positioned at the end of the barrel that provides the resulting tubing its shape and dimension. Thus, the function of this extrusion die is to shape the molten plastic exiting the extruder into its desired cross-sectional shape.

For tubing, an annular shape is required. A mandrel is suspended in the center of a circular passage in the housing mounted to the end of the extruder barrel. Special metal bridges called "spiders" hold the mandrel (also called a "torpedo") securely in place. An inner die (also called a "die pin") mates with the downstream end of the mandrel, and forms the inside diameter of the polymer tubing. An air hole running through the die pin allows passage of air through the die body to the interior of the melt tube. A slight positive air pressure keeps the inner diameter of the tubular extrudate from collapsing as it exits the extruder die.

Meanwhile, an outer die (also called a "die land") is mounted to the housing to form the outer diameter of the tubular extrudate. This die land can be changed to create tubes of different outside diameters or wall thickness, while maintaining the original die pin in place. A retaining plate attached to the housing secures the die land and die pin in their proper position. Thus, it is this combination of the die pin and die land that produces the proper tube shape and wall thickness as the polymer melt is forced through the gap between the two dies to form the tubular extrudate.

Figure 8:
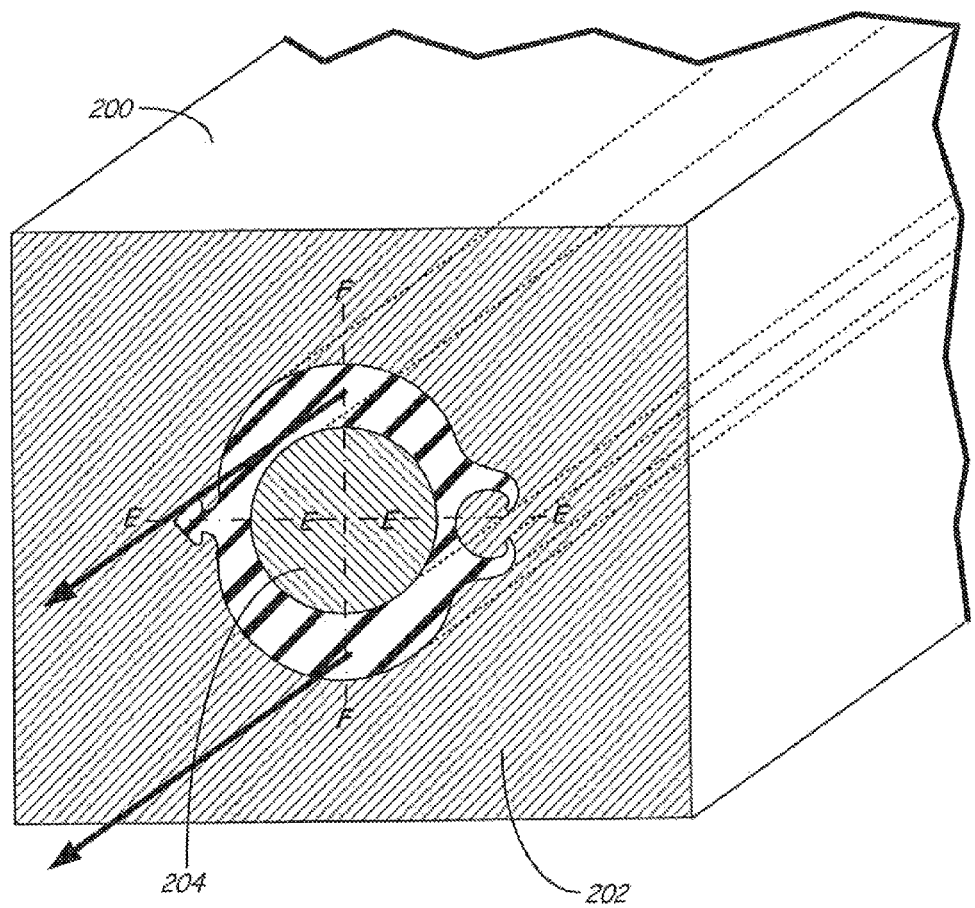
FIG. 8 is a perspective view of the extruder housing showing the inner and outer die plates.

For purposes of the extruder die housing 200 for the protective tubing assembly 10 of the present invention, as shown in FIG. 8, the die land 202 should have an oblong interior surface to produce the oblong exterior shape of the tubular body 12. The die land will also feature the required surface recess features to produce the male projecting connector 66 and female receiving connector 90 that are integrally attached to the exterior surface of the extruded tubular body 12. At the same time, a round bore 30 is desired in the tubular body 12 to prevent the catheter or other protected object from binding inside the bore. Conventional wisdom in the industry calls for a die pin featuring a round circular outside surface to produce a corresponding cylindrical bore in the extruded tubular body 12. It has been found, however, that as the tubular extrudate cools, the annular material stretches to yield an undesirable oblong shape bore. Surprisingly, it has been discovered that an oblong-shaped inner surface on a die pin 204 will produce a tubular extrudate having a round inside diameter and cylindrical bore after the tubing cools. More preferably, the longitudinal axis E-E along this die pin 204 should be positioned substantially transverse to the longitudinal axis F-F of the oblong-shaped die land 202, as depicted in FIG. 8. This unusual arrangement of oblong-shaped die pin 204 and die land 202 at substantially 90° angles to each other produces the desired tubular body 12 having in its cross-section a round, inside diameter and oblong, outside diameter providing the cylindrical-shaped bore 30 and extra wall thickness Z along the longitudinal axis A-A shown in FIG. 4.

The above specification and data provide a complete description of the protective tubing assembly of the present invention. But many other embodiments of the invention can be made without departing from the spirit and scope of the invention. For example, larger diameter tubing for larger objects can be sued in this invention while retaining the asymmetrical cross-section, increased wall thicknesses, integral male and female connectors, and substantially flat exterior bearing surfaces for securing the tubing in a connected, coiled state with a substantially flat planar alignment. The invention of this Application therefore resides in the claims hereinafter appended.

I claim:

1. A protective tubing assembly for packaging an elongated flexible protected object, the protective tubing assembly comprising:
   (a) a flexible tubular body that is capable of being coiled;
   (b) the tubular body having an asymmetrical cross section having a longitudinal axis and a transverse axis, such asymmetrical cross-section comprising:
      (i) an elongate outside perimeter having a longer outside diameter along the longitudinal axis than its outside diameter along the transverse axis;
      (ii) an uniform inside diameter forming a bore along the length of the tubular body;
      (iii) a greater wall thickness along the longitudinal axis than its wall thickness along the transverse axis;
   (c) a male projecting member extending outwardly from the tubular body along the transverse axis and longitudinally along at least a substantial portion of the length of the tubular body;
   (d) a female concave-shaped receiving member extending outwardly from the tubular body along the transverse axis in a diametrically opposed position from the male projecting member, the female receiving member extending along a substantial portion of the tubular body;
   (e) wherein the female receiving member is positioned and proportioned to receive the male projecting member of another portion of the tubular body in a connected relation when the tubular body is coiled to retain the tubular body in its coiled, substantially planar arrangement; and
   (f) wherein the increased wall thickness of the tubular body along the longitudinal axis helps to reduce twisting of the tubular body when in its coiled arrangement to inhibit the elevation of one of the tubular coiled windings from the substantially planar coiled arrangement.

2. The protective tubing assembly of claim 1, wherein the male projecting, member defines the shape of an arrowhead in cross section.

3. The protective tubing assembly of claim 1, wherein the male projecting member defines the shape of a half moon on a throated neck in cross section.

4. The protective tubing assembly of claim 1, wherein the male projecting member defines the shape of a rectangle or square on a throated neck in cross section.

5. The protective tubing assembly of claim 1, wherein the male projecting member defines the shape of a half star on a throated neck in cross section.

6. The protective tubing assembly of claim 1, wherein the female receiving member is C-shaped in cross section.

7. The protective tubing assembly of claim 1, wherein the male projecting member and female receiving member are dimensioned and shaped with respect to each other so that an audible snapping sound is produced when the male projecting member is inserted into the female receiving member in connected relationship.

8. The protective tubing assembly of claim 1, wherein the wall thickness of the tubular body along the longitudinal axis is at least about 0.035 inches.

9. The protective tubing assembly of claim 1, wherein the length of the female receiving member extending outwardly from the tubular body is sufficiently small so that when the tubular body is coiled with the male projecting member retained inside the female receiving member, adjacent connected coils are close together to reduce rotation of the one coil with respect to the other coil.

10. The protective tubing assembly of claim 9, wherein the length of the female receiving member is less than about one inch.

11. The protective tubing assembly of claim 1 further comprising substantially flat exterior surfaces on the tubular body Where the male projecting member joins the tubular body, and where the female receiving body joins the tubular body, so that when the tubular body is connected in the coiled arrangement, the respective flat exterior surfaces along adjacent coils are within dose proximity with each other to reduce rotation of one coil with respect to the other coil to enhance the stability of the coiled arrangement.

12. The protective tubing assembly of claim 1 further comprising a first substantially flat exterior surface on the tubular body where the male projecting member joins the tubular body, and a second substantially flat exterior surface along the outside of the female receiving member, so that when the tubular body is connected in coiled arrangement, the first substantially flat exterior surface on the tubular body is within close proximity with the second substantially flat exterior surface on the female receiving member to reduce rotation of one coil with respect to the other coil to enhance the stability of the coiled arrangement.

13. The protective tubing assembly of claim 1, wherein the protected object carried inside the bore is a catheter.

14. The protective tubing assembly of claim 1, wherein the protected object carried inside the bore is a guidewire.

15. The protective tubing assembly of claim 1, wherein protected object carried inside the bore is an elongated flexible article of manufacture.

16. The protective tubing assembly of claim 1, which is extruded in its manufacture using an extruder housing having an inner die pin and an outer die land forming the inside diameter and outside diameter of the tubular body extrudate.

17. The protective tubing assembly of claim 16, wherein the outer die land has an elongate shape for forming the elongate outside perimeter of the tubular body.

18. The protective tubing assembly of claim 16, wherein the inner die pin has an elongate shape forming a circular inside diameter on the tubular body once it cools.

19. The protective tubing assembly of claim 18, wherein the elongate-shaped inner die pin having a longitudinal axis is positioned so that its longitudinal axis is transverse to a longitudinal axis along the elongated shaped outer die land.

* * * * *

UNITED STATES PATENT AND TRADEMARK OFFICE
CERTIFICATE OF CORRECTION

| | | |
|---|---|---|
| PATENT NO. | : 8,397,911 B1 | Page 1 of 1 |
| APPLICATION NO. | : 13/563304 | |
| DATED | : March 19, 2013 | |
| INVENTOR(S) | : Todd J. Bauman | |

It is certified that error appears in the above-identified patent and that said Letters Patent is hereby corrected as shown below:

In the Claims:

Column 11, line 43 (Claim 2) "male projecting, member defines the shape of an arrowhead in" should be -- male projecting member defines the shape of an arrowhead in --

Column 12, line 23 (Claim 11) "adjacent coils are within dose proximity with each other to reduce" should be -- adjacent coils are within close proximity with each other to reduce --

Signed and Sealed this
Fourth Day of June, 2013

Teresa Stanek Rea
*Acting Director of the United States Patent and Trademark Office*